United States Patent [19]
Gloyd et al.

[11] Patent Number: 5,616,115
[45] Date of Patent: Apr. 1, 1997

[54] HEATED HUMIDIFIER FOR INCUBATOR

[75] Inventors: David A. Gloyd, Columbia; Emigdio A. Uribe, Marriotsville; Robert J. Koch, Ellicott City; Harry E. Belsinger, Jr., Baltimore, all of Md.

[73] Assignee: Ohmeda Inc., Liberty Corner, N.J.

[21] Appl. No.: 583,203

[22] Filed: Jan. 4, 1996

Related U.S. Application Data

[63] Continuation of Ser. No. 259,829, Jun. 15, 1994, abandoned.

[51] Int. Cl.[6] ................................................. A61B 16/00
[52] U.S. Cl. ............................................................. 600/22
[58] Field of Search ............................... 600/22; 165/60; 261/142, 153, 156, 150, 149, 119.1; 55/95, 96

[56] References Cited

U.S. PATENT DOCUMENTS

| | | | |
|---|---|---|---|
| 1,839,234 | 1/1932 | Lehn | 261/153 |
| 3,311,355 | 3/1967 | Rait | 261/2 |
| 3,355,155 | 11/1967 | Heltzen et al | 261/130 |
| 3,584,193 | 6/1971 | Badertscher | 261/142 X |
| 3,821,947 | 7/1974 | Schossow | 600/22 |
| 4,003,967 | 1/1977 | Potvin | 261/30 |
| 4,564,746 | 1/1986 | Morton et al. | 261/142 X |
| 4,604,246 | 9/1986 | Choe | 261/71 |
| 4,796,605 | 1/1989 | Sasaki et al. | 600/22 |

Primary Examiner—Angela D. Sykes
Assistant Examiner—Samuel Gilbert
Attorney, Agent, or Firm—Roger M. Rathbun; R. Hain Swope

[57] ABSTRACT

A heated humidifier for an infant incubator wherein the water in the water reservoir is heated by an active heater located above the surface of the water and a heat exchanger that transfers heat from the active heater and which extends downwardly to a point beneath the water surface to heat the water. In the preferred embodiment, the heat exchanger is an extruded member in the shape of an I-beam to transfer the heat from an electric heater above the surface of the water to heat the volume of water in the reservoir to create water vapor.

2 Claims, 5 Drawing Sheets

HEATED HUMIDIFIER FOR INCUBATOR

This is a continuation of application Ser. No. 08/259,829 filed Jun. 15, 1994 now abandoned.

BACKGROUND OF THE INVENTION

This invention relates to infant incubators and, more specifically, to a heated humidifier for humidifying the air delivered to the infant compartment within which the infant is positioned.

Generally it is advantageous to humidify the heated air that is delivered to an infant compartment in caring for that infant and current incubators provide various methods of carrying out that humidification.

One type of humidifier currently in use with infant incubators utilizes a passive water supply that is not heated and the warm air is passed over the surface to pick up the water vapor. This type of humidifier is, however, not extremely efficient since the lack of active heating of the water in the humidifier limits considerably the amount of water vapor that is available to be picked up by the stream of air delivered to the infant compartment. In addition, such humidifiers are also very dependent upon the particular setting of the incubator, the ambient temperature and the humidity of the nursery within which the incubator is located.

Another type of humidifier for humidifying such air is shown and described in Air Shields U.S. Pat. No. 5,242,375 and which includes a flat heater positioned beneath an evaporation tray to heat the water to enhance the release of vapor for introduction into the air stream delivered to the infant. It is quite typical to utilize such heaters positioned beneath the volume of water to heat the water and where the heated stream of air to the patient is first passed over the upper surface of the heated water where it picks up the water vapor to deliver the humidified air to the infant.

Again, however, there are shortcomings of the beneath the water reservoir arrangement. First, the water reservoir must be a fairly substantial volume to avoid the continual depletion of the water and thus the need for attending personnel to continuously refill the reservoir. Due to the large volume of water, therefore, the entire volume must be heated from the bottom, thus a considerable amount of energy is required and the response time to changes desired in the degree of humidification is fairly long. The control loop is relatively long and overshoots in humidity are common.

Additionally, with the heater located beneath the reservoir, the container for holding the quantity of water must be a specialized container since the bottom of the container must be of a good heat conductive material. The preferable material for reservoir containers is plastic that is relatively transparent so that the user can visually ascertain the level of the water. Also, of course, a molded single piece plastic container is inexpensive to produce.

A problem is, therefore, that the plastic containers cannot be directly heated through a plastic bottom and therefore such containers require a heat conductive material such as metal to actually transmit the heat into the water. Such containers, therefore, must be made of different material, that is, plastic sides with a metallic bottom, and the juncture between the metal material and the plastic material is a potential source of leaks and causes problems in removal for cleaning. Also, obviously, the addition of a special material at the bottom of the reservoirs creates additional expense over that of producing the entire reservoir container from a single, transparent, moldable plastic material.

Accordingly, apart from the inefficiencies of providing heat to the very bottom of the large volume of water where the water vapor is being generated and removed from the upper surface only of the reservoir, the construction of the reservoir container is fairly costly and specialized, requiring a heat conductive bottom to allow the flow of heat into the water.

SUMMARY OF THE INVENTION

The present invention provides an improved heated humidifier for use with an infant incubator and which has good response time by locating the active heater above the surface of the water and then providing a heat exchanger that depends downwardly into the water.

In this way, the unit is efficient since the heating is not limited to heating the entire volume of water from the bottom of the container. Therefore humidity is generated at a reasonably fast rate. In addition, by providing the active heater above the surface of the water with a heat exchanger extending downwardly beneath the surface of the water, the humidifier is capable of good response to changes in set points, reservoir refills, incubator start-ups and perturbation of the incubator since it is not necessary to heat up the entire volume of water from the bottom of the container in order to achieve the intended results.

Further, the active heater may be an electrical heater since it is safely positioned above the surface of the water and therefore is not in contact with the water. The heat is transmitted to the water by the conductive heat exchanger protrudes downwardly into the water. The unit is therefore satisfactory from a safety standpoint since no electrical connections or heating elements actually are immersed in the water.

Further, the reservoir container may thus be readily manufactured of the same plastic material throughout, thus may be molded as a one piece container of a transparent material. No special heat conductive material need be included at the bottom of the container and thus the container is leak-free and can be produced relatively inexpensively.

Other features of the heated humidifier will become more apparent in light of the following detailed description of a preferred embodiment thereof and as illustrated in the accompanying drawings.

BRIEF DESCRIPTION OF THE DRAWINGS

FIG. 3A is an isometric view of one of the components of the heated humidifier of FIG. 3.

DESCRIPTION OF THE PREFERRED EMBODIMENT

Figure 1:
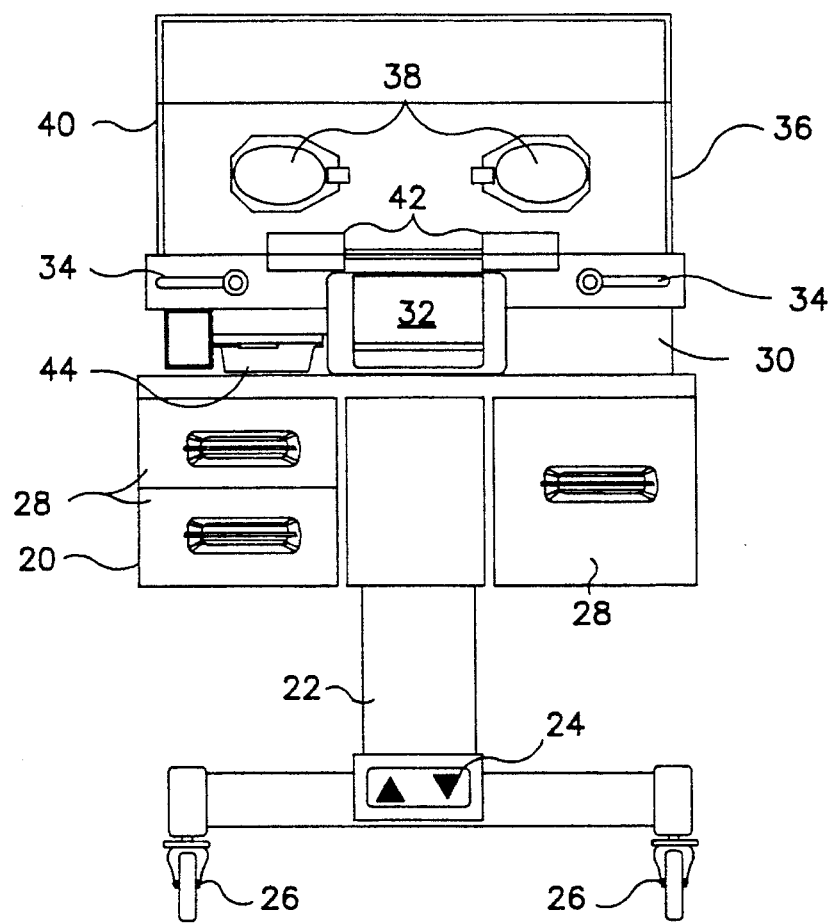
FIG. 1 is a front view of an incubator having incorporated therein a heated humidifier constructed in accordance with the present invention.

Referring now to FIG. 1, there is shown an infant incubator 20 mounted upon a base frame 22. The base frame 22 provides support for the infant incubator 20 and may be adjustable in height by control 24 and generally may include wheels 26 so that the infant incubator 20 can be easily be moved from one position to another. The base frame 22 may include storage facility for holding products used in attending to infants and, as shown, drawers 28 are provided for access to facilitate such storage.

Infant incubator 20 includes a base 30, preferably of a rigid structural material such as aluminum or a plastic material such as polycarbonate. The base 30 rests upon the base frame 22 and contains much of the functioning mechanisms for operation of the infant incubator 20.

Base 30 may also include a control panel 32 where controls are located for operating the infant incubator 20. Such controls may include temperature settings, temperature read-outs, alarm limits and the like. Various levers 34 are part of the base 30 and are used to adjust the position of the infant platform (not shown) on which the infant rests.

A hood 36 overlies base 30 and encloses therein an infant compartment and is preferably of a transparent material such as plexiglass for viewing the infant. The hood 36 has portholes 38 for the attending personnel to gain ready access to the infant. A further large access door 40 is also provided to insert and remove the infant or to carry out various procedures on the infant. Access door 40 is pivoted outwardly on hinges 42.

A heated humidifier 44 is positioned within the base 30 and, as will be explained, is removable therefrom.

Figure 2:
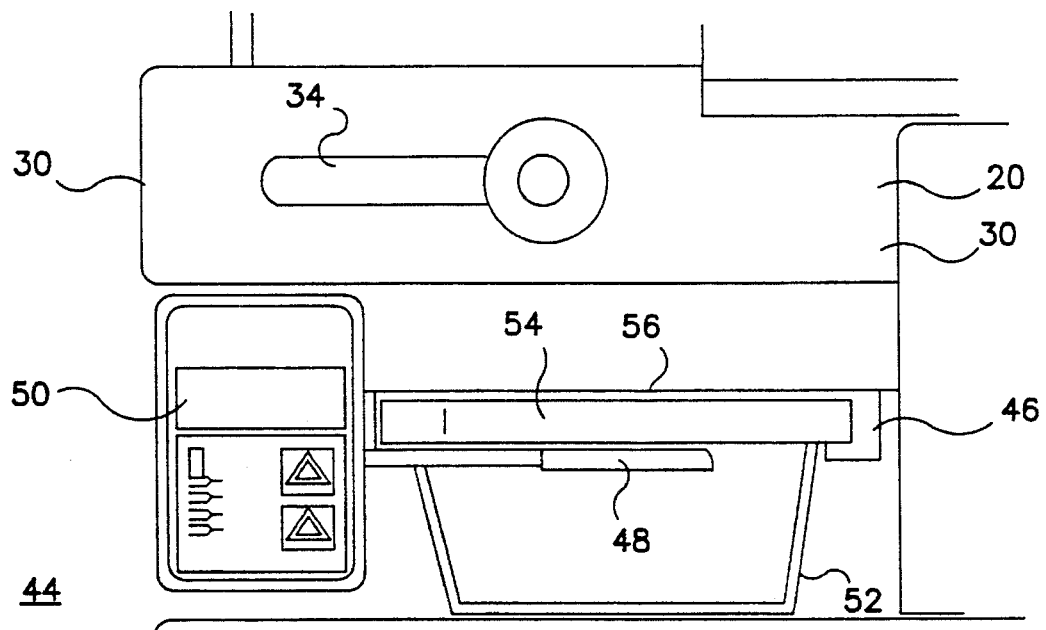
FIG. 2 is an enlarged front view showing more details of the humidifier of the present invention.

Turning now to FIG. 2, there is shown an enlarged schematic view of the heated humidifier 44 constructed in accordance with the present invention. As can be seen, the heated humidifier 44 is affixed to the infant incubator 20 by sliding the heated humidifier 44 on a pair of L-shaped flanges 46 which depend downwardly from base 30, only one of which is shown in FIG. 2. The heated humidifier 44 can thus be readily be installed or removed from the infant incubator 20 for cleaning, maintenance and the like. An optional lever mechanism 48 may be used to retain the heated humidifier 44 in its installed position to prevent it from becoming inadvertently dislodged from its operative position.

A humidifier control panel 50, is provided on the heated humidifier 44 and may include various read-outs, such as relative humidity, low water level indicator and may also contain the control for setting the desired humidity setting as well as other warning and/or alarm functions.

A water reservoir 52 contains the water to be used for humidification of the air passing to the infant and is preferable a transparent plastic construction so that the user can easily view the inside volume of the reservoir to determine the quantity of water contained therein. By this means, the user can insure visually that the water level is within the desired range of levels needed for operation of the heated humidifier 44. On top of the water reservoir 52 is a cover 54 and a grommet 56 can be seen that seals the inlet of the heated humidifier 44 to a passageway within the infant incubator 20 that delivers heated air at a positive pressure to the inside of hood 36 for administration to the infant contained therein.

Figure 3:
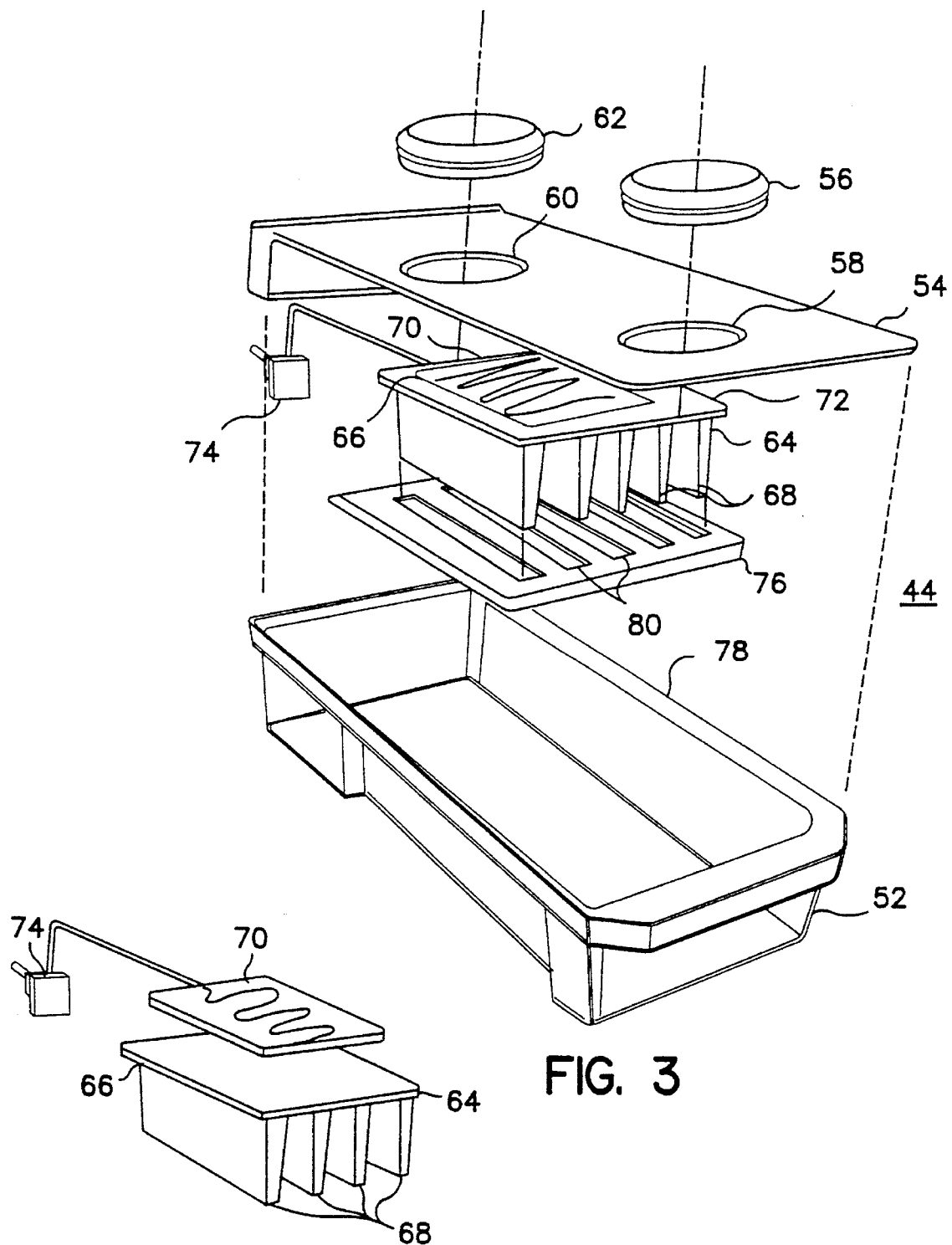
FIG. 3 is an exploded view showing the individual components of the heated humidifier constructed in accordance with the present invention.

Turning now to FIG. 3 and FIG. 3A, there is shown, respectively, an exploded view of a heated humidifier 44 and an isometric view of one of the components of the heated humidifier 44 constructed in accordance with the present invention. As noted, the water reservoir 52 is a container for holding the volume of water to be vaporized to create the humidification for the infant. The cover 54 encloses the top of the water reservoir 52 and has an inlet opening 58 and an outlet opening 60. In operation, heated air from the conventional blower/heater mechanism of the infant incubator enters the inlet opening 58 and exits the heated humidifier 44 through the outlet opening 60 where it is then directed by passages in the incubator itself to enter the enclosed compartment wherein the infant is positioned.

A pair of grommets, 56 and 62, provide sealing between the inlet opening 58 and the outlet opening 60, respectively, to the various passages of the infant incubator. The inlet grommet 56 and outlet grommet 62 provide an automatic seal as the heated humidifier 44 can be slid into and out of its operative position within the incubator. Thus, even though the grommets 56, 62 provide a good seal, they are readily disengaged by the user merely sliding the heated humidifier 44 out of its position to remove the same from the infant incubator 20.

A heat exchanger 64 is provided to heat the upper surface of the water contained within water reservoir 52 and heat exchanger 64 is preferably a flat plate 66 with a plurality of fins 68 depending downwardly into the water when in its operative position. The heat exchanger 64 may be an aluminum extrusion, however, various materials that are good heat conductors may be utilized for the application.

An electric heater 70 provides heat to the heat exchanger 64. In the preferred embodiment, electric heater 70 is a flat resistance heater that is bonded to the upper surface of the flat plate 66 and thus is protected from contact with the water contained within water reservoir 52. A sealing gasket 72 may be necessary to insure that the electric heater 70 is protected from the water. Gasket 72 surrounds the periphery of the electric heater and seals against the lower surface of cover 54. Conventional means, such as an electrical connector 74 provides power to the electric heater 70 and various conventional controls may be used to establish the desired set temperature so that the proper amount of humidification can be selected and maintained.

A mounting plate 76 that fits within the upper edge 78 of the water reservoir 52 holds the heat exchanger 64 in its proper position such that the electric heater 70 is maintained well clear of the water and only the fins 68 of the heat exchanger 64 depend downwardly into the water for heating the surface of the water. As can be seen, mounting plate 76 has a plurality of openings 80 through which the fins 68 pass. Mounting plate 76 also reduces the heating effect that the electric heater 70 may have directly on the air passing through the humidifier.

Figure 4:
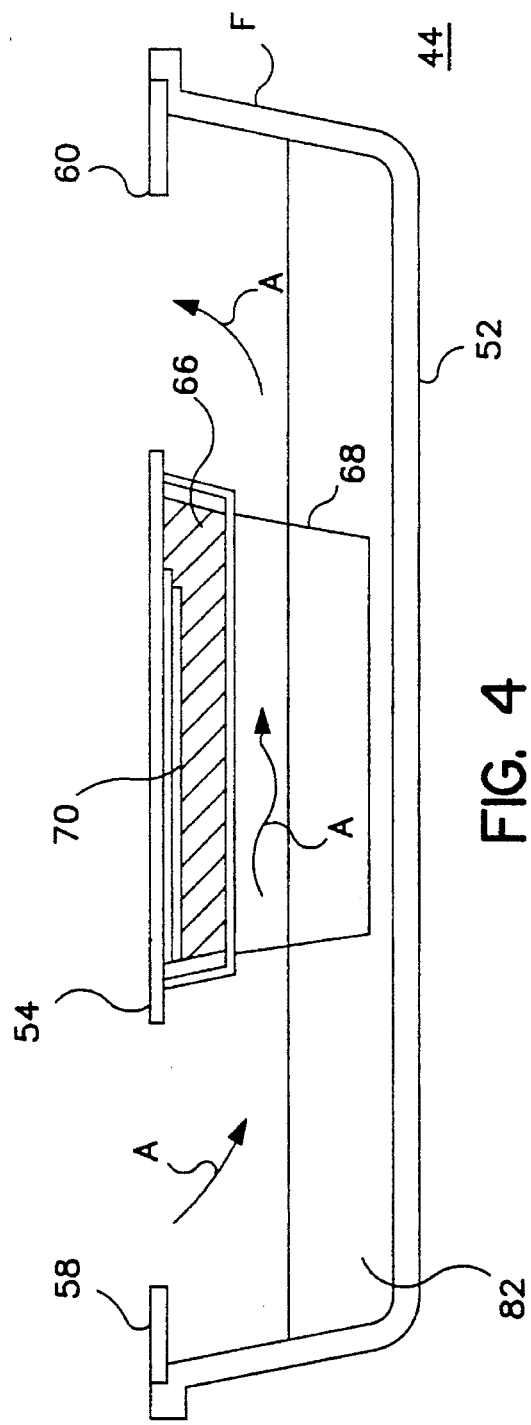
FIG. 4 is a side schematic view showing the air flow through the humidifier of the present invention.
Figure 5:
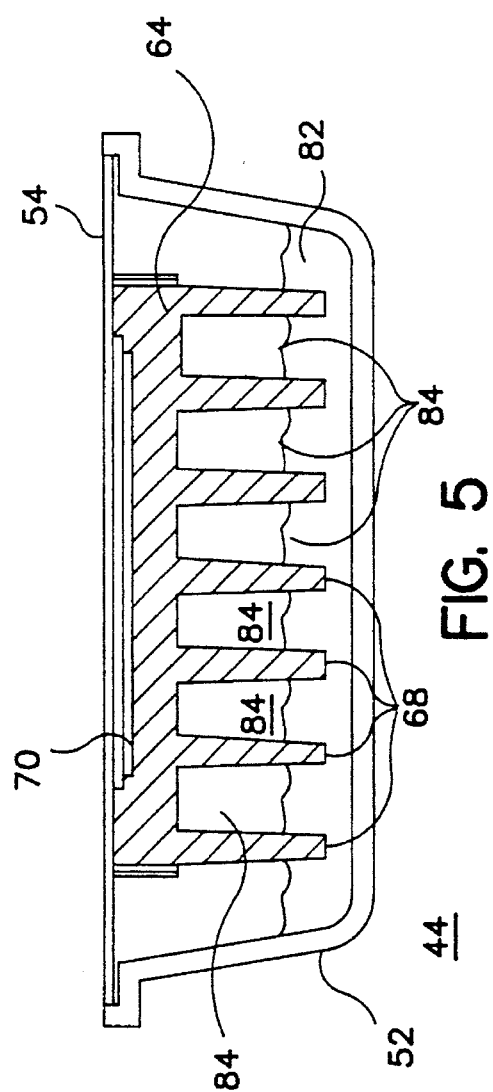
FIG. 5 is an end schematic view showing the heater surfaces used in the heated humidifier of the present invention.

Turning now to FIGS. 4 & 5, there is shown schematic views, taken from the side and the end of the heated reservoir 44 constructed in accordance with the present invention and which may be used to explain the unique operation of the apparatus. Heated air from the infant incubator system is introduced into the heated humidifier 44 through the inlet opening 58, passes along the surface of the water 82 contained within water reservoir 52 and exits the heater humidifier 44 through outlet opening 60. As the air passes therethrough, it picks up the water vapor created at the surface of the water 82 and thus humidifies the air that ultimately exits from the heated humidifier 44.

The surface of the water 82 is heated to promote the formation of the vapor by the plurality of fins 68 that extend downwardly into the water 82 and which are part of the heat exchanger 64. The heat exchanger 64 itself is actively heated by the electric heater 70 located on the top surface of flat plate 66 such that the electric heater 70 is protected from contact with the water 82. As can be seen particularly in FIG. 5, the fins 68 create a plurality of individual passageways 84 and which are filed with water vapor from the heated water 82. Those individual passageways 84 provide efficient humidification to the air passing therethrough in the direction of the arrows A since the water vapor is trapped into fairly small volumes and is readily picked up by the heated air passing along those individual passageways 84.

Accordingly, the heated humidifier 44 has the advantage of heating the surface of the water 82 contained within water reservoir 52 rather that heating the entire volume of water to create the water vapor at the surface. Thus the response time is rapid and the humidity control loop is shorter as opposed to having a heater positioned at the bottom of a water reservoir.

Figure 6:
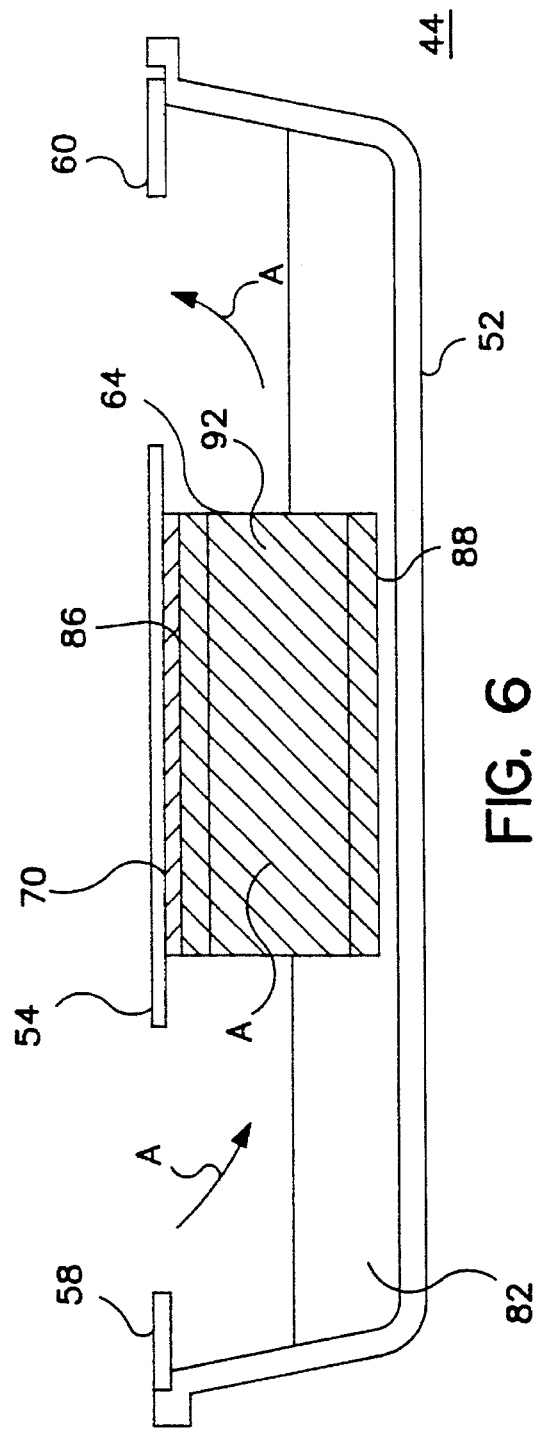
FIG. 6 is a side schematic view showing a alternate embodiment of the humidifier of the present invention.
Figure 7:
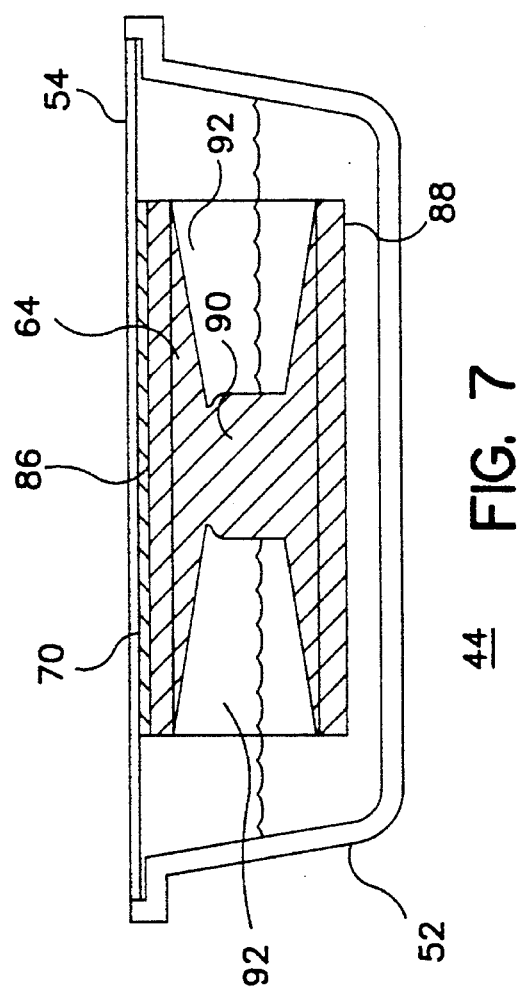
FIG. 7 is an end schematic view showing the alternate embodiment of the FIG. 6 humidifier.

An alternate embodiment of the heated humidifier 44 of the present invention is shown in FIGS. 6 and 7 which show, respectively, side and end schematic views of the alternate embodiment and showing the flow paths therethrough. In these FIGS., the heat exchanger 64 is in the general shape of an I-beam and has certain advantages over the prior FIGS. 4 & 5 embodiment by reducing the surface area of the heat exchanger located above the water and which is exposed to the air passing through the humidifier.

One of the problems in the prior embodiment is that the downwardly depending fins 68 can cause direct heating of the air passing through the humidifier and which may affect the temperature of the air entering the incubator to reach the infant. Since the incubator main heater and heater controls are elsewhere in the incubator, the intent of the humidifier is to humidify the air passing through that humidifier without unduly causing an elevation of the temperature of that air. Otherwise, the humidifier could cause a noticeable effect on the temperature of the air that enters the infant compartment and make accurate regulation of that temperature more difficult.

Therefore, with the heat exchanger shaped as an I-beam in the FIG. 6 and 7 embodiment, the heat transmitted to the passing air above the surface of the water is minimized and more of the heat enters the water where the heat is intended to be utilized.

A drawback, however, of the I-beam shape is that the response time is longer than that of the prior FIGS. 4 & 5 embodiment since there is less of a surface heating phenomenon and the heat is introduced into the water at a greater depth.

In this embodiment the I-beam has an upper flat or planar surface 86 and a lower flat or planar surface 88 and, of course, a reduced area 90 intermediate the upper planar surface 86 and lower planar surface 88.

The upper planar surface 86 may be directly affixed to the cover 54 by conventional means such as an adhesive or mechanical fixtures and the electric heater 70 may conveniently be sandwiched in between the cover 54 and the upper planar surface 86 and thus provide heat to the heat exchanger 64 in an area above the surface of the water 82. Again, as in the FIG. 4 & 5 embodiment, the heat exchanger 64 may be an extruded aluminum part, and again, the lower portion of the heat exchanger 64 enters into and projects downwardly beneath the surface of the water 82. In this case, the lower planar surface 88 rests beneath the surface of the water 82 and two passageways 92 are formed through which the air passes.

As shown in the alternate embodiment, the air progresses through the heated humidifier 44 generally in the direction of arrows A from the point it is introduced thereto through inlet opening 58, along the passageways 92 and emerges as humidified air at the outlet opening 60 to enter the stream of air flowing through the infant incubator.

Figure 8:
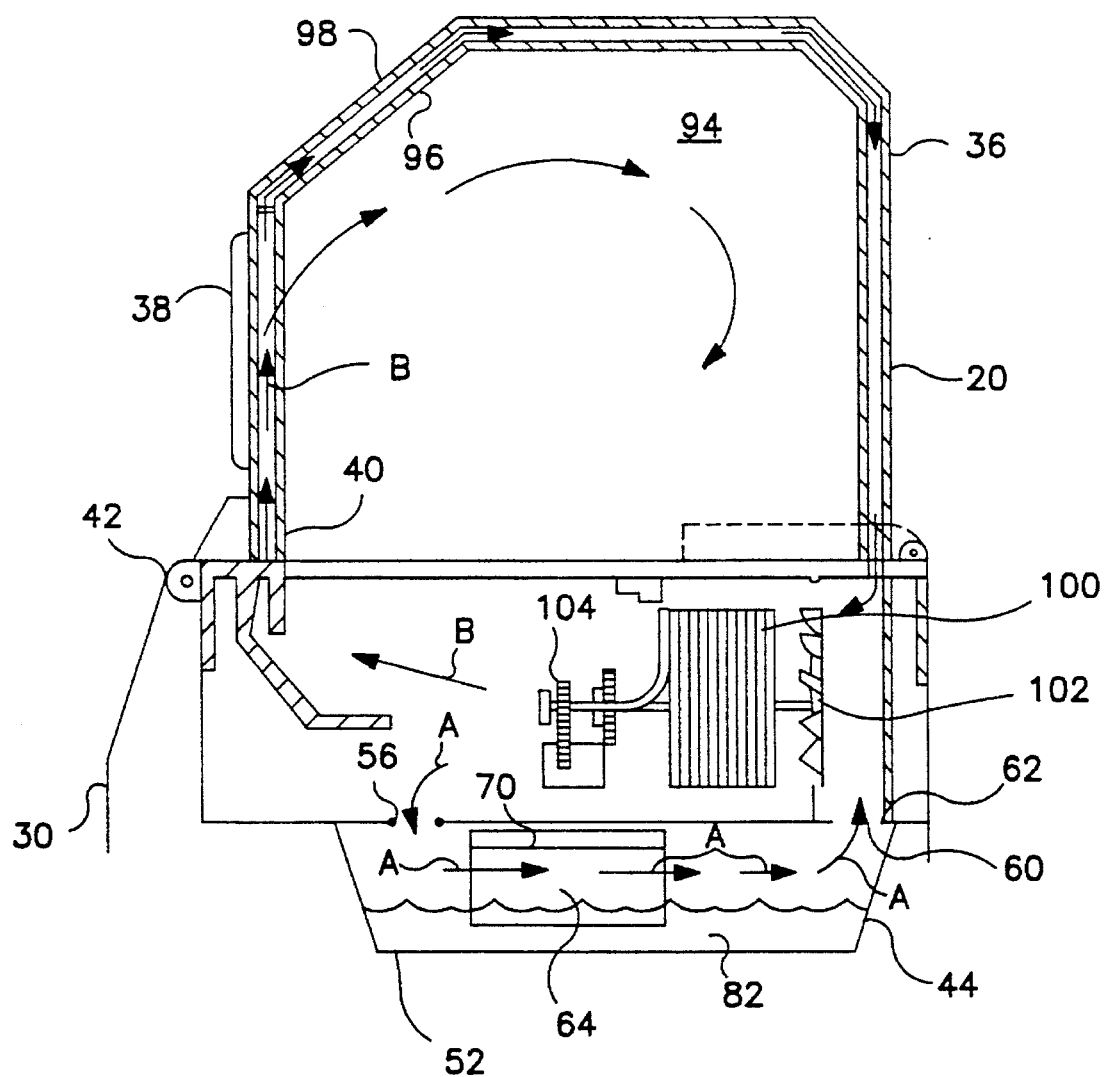
FIG. 8 is a side schematic view showing an infant incubator having a heated humidifier constructed in accordance with the present invention.

Turning finally to FIG. 8, there is shown a schematic of an infant incubator 20 and which includes the heated humidifier 44 of the present invention. The incubator 20 is basically of the design shown and described in U.S. Pat. No. 4,936,824, issued Jun. 26, 1990 and therefore will only be briefly described herein. In particular, the incubator 20 includes the hood 36 that surrounds and encloses therein the infant compartment 94 within which the infant is located. In the preferred embodiment, hood 36 is of a double wall construction in which an inner wall 96 and an outer wall 98 form a passageway through which heated air circulates in the directions of the arrows B.

Within the base 30 of incubator 20, there is located the means to heat and circulate the air through the hood 36 and which includes a conventional heater 100 and a fan 102 that induces the flow of air from the rear of the hood 36 past the heater so that the circulated air is thus heated and then reintroduced into the hood 36 at the front of the incubator 20. The fan 102 is, of course powered by an electric motor 104 and which is controlled in accordance with the disclosure of the aforementioned U.S. Patent.

As indicated, however, the main flow pattern is in the circulation of air in accordance with the arrows B. A separate sidestream is accomplished for use of the heated humidifier 44 and that flow of is generally in accordance with the arrows A (FIG. 6). The flow of air for the humidifier 44 thus enters the humidifier 44 through the inlet opening 58 which withdraws a portion of the main stream of air moving through the incubator 20. That flow through the inlet opening 58 is created by the path of least resistance, that is, there is a certain resistance in the flow of air along the arrows B and in entering the double wall hood 36 at the front of the incubator 20. Some of the air, therefore naturally seeks an alternative flow path and which is provided by the path through the heated humidifier 44.

Accordingly, that portion of air, passes through humidifier 44, along the surface of the water 82 and picks up the water vapor at the surface of the water as previously described. The heat exchanger 64 provides the heat to the water at or near the surface thereof to create the water vapor and, as has been explained, the heat exchanger 64 is heated by an electric heater 70 located above the surface of the heater.

The thus humidified air then reenters the main stream of air by reentering the base 30 through the outlet opening 60 located on the negative side of the fan 102 and which assists in continuing the flow of air through the humidifier 44. The humidifier 44 thereby provides a source of humidity to the main stream of air in the flow stream depicted by the arrows B. As is noted, although the main flow of air is contained within the double walled hood 36, some of that air enters the infant compartment and therefore reaches the infant.

As can be seen, therefore, the humidifier 44 is used in a continuous bypass stream of air that humidifies the air to the infant and which adds that humidified stream to the main flow of air to the infant for humidifying the infant compartment 94.

It will be understood that the scope of the invention is not limited to the particular steps or materials disclosed herein, by way of example, but only by the scope of the appended claims.

We claim:

1. An incubator for containing an infant, said incubator comprising:

a base section having an infant support adapted to underlie and support the infant;

a hood mounted upon said base section and forming an infant compartment therein for containing the infant;

an air moving means in said base section adapted to move air from said base section into said infant compartment to reach the infant;

a heated humidifier for humidifying the air supplied by said air moving means from said base section to said infant compartment; said humidifier having a reservoir containing a quantity of water therein, said humidifier further having an inlet for receiving air from said air moving means and an outlet for discharging humidified air, and having a passageway within said humidifier between said inlet and said outlet passing the air along the surface of the water, heater means within said humidifier to provide localized heating of the water at or near the surface of the water to cause the formation of water vapor at the surface of the water, said heater means comprising a heat exchanger having an upper flat, planar surface located above and parallel to the surface of the water, said upper flat, planar surface having at least one fin extending downwardly from said upper flat, planar surface into and below the surface of the water and an active flat electric heater contacting said upper flat, planar surface of said heat exchanger to provide heat to said heat exchanger at said upper flat, planar surface of said heat exchanger above the surface of the water; and ducting means directing at least a portion of the air passing from said base section to said infant compartment through said passageway of said humidifier to cause humidified air to enter said infant compartment to reach the infant.

2. An infant incubator as defined in claim 1 wherein said heat exchanger including said at least one fin has a cross section in a shape of an I-beam.

\* \* \* \* \*